(12) United States Patent
Mantz

(10) Patent No.: US 6,253,767 B1
(45) Date of Patent: Jul. 3, 2001

(54) GAS CONCENTRATOR

(76) Inventor: Robert F. Mantz, 2350, Woodlawn Cir. East St. Petersburg, FL (US) 33704

( * ) Notice: Subject to any disclaimer, the term of this patent is extended or adjusted under 35 U.S.C. 154(b) by 0 days.

(21) Appl. No.: 09/210,413

(22) Filed: Dec. 10, 1998

(51) Int. Cl.$^7$ ................................................ A61M 16/00
(52) U.S. Cl. ........................ 128/205.13; 128/205.14; 128/205.15; 128/205.16; 128/205.17
(58) Field of Search ...................... 128/205.13, 205.14, 128/205.15, 205.16, 205.17

(56) References Cited

U.S. PATENT DOCUMENTS

| | | | |
|---|---|---|---|
| D. 335,552 | 5/1993 | Kohnke | D29/7 |
| D. 363,774 | 10/1995 | Robertson, II et al. | D24/110 |
| 3,741,250 | * 6/1973 | Mercier | 138/30 |
| 4,022,202 | 5/1977 | Price | 128/145.8 |
| 4,106,502 | 8/1978 | Wilson | 128/145.8 |
| 4,121,580 | 10/1978 | Fabish | 128/145.7 |
| 4,374,521 | 2/1983 | Nelson et al. | 128/205.13 |
| 4,506,667 | 3/1985 | Ansite | 128/204.25 |
| 4,682,591 | 7/1987 | Jones | 128/204.25 |
| 4,764,346 | * 8/1988 | Lewis et al. | 422/120 |
| 4,870,962 | 10/1989 | Sitnik | 128/205.13 |
| 5,067,497 | 11/1991 | Greear et al. | 128/207.15 |
| 5,140,982 | 8/1992 | Bauman | 128/205.13 |
| 5,163,424 | 11/1992 | Kohnke | 128/205.13 |
| 5,217,006 | 6/1993 | McCulloch | 128/205.13 |
| 5,359,998 | 11/1994 | Lloyd | 128/203.11 |
| 5,483,955 | 1/1996 | Morris | 128/205.13 |
| 5,540,221 | 7/1996 | Kaigler et al. | 128/205.13 |
| 5,546,934 | * 8/1996 | Kaigler et al. | 128/205.13 |
| 5,558,371 | 9/1996 | Lordo | 285/114 |
| 5,632,269 | 5/1997 | Zdrojkowski | 128/204.23 |
| 5,647,354 | 7/1997 | Lakhani et al. | 128/205.13 |
| 5,701,883 | 12/1997 | Hete et al. | 128/204.26 |

OTHER PUBLICATIONS

Ambu, "Ambu® Disposable . . . Because you don't get a second chance to save a life" (1 page).
Lifeguard Medical Products, Inc., "Lifeguard Disposable Manual Resuscitator" (1 page).
Lifeguard Medical Products, Inc., "Lifeguard Disposable Anesthesia Respiratory Filter" (1 page).
Lifesaver® II Manual Resuscitation Kit No. 5270, Hudson, 1986 (3 pages).
Mercury Medical "Specializing in Anesthesia, Respiratory and Critical Care Products" (2 pages).
Mercury Medical "Now You Can Pat Our Engineers on the Back Instead Of Your Patients" (2 pages).
Infant Resuscitator from Fraser Harlake (1 page).
Baxter "Resuscitation Devices" (1 page).
"The Hope resuscitator belongs in place like these . . . " (1 page).
Manual Resuscitator Air viva II (1 page).
Puritan Bennett "Affordable Quality at a Disposable Price" (5 pages).

(List continued on next page.)

Primary Examiner—Aaron J. Lewis
Assistant Examiner—Mital Patel
(74) Attorney, Agent, or Firm—Holland & Knight LLP

(57) ABSTRACT

A gas concentrator adaptable for use within a breathing apparatus, particularly for use within a resuscitator, Trach T, patient tee, or a high oxygen concentration mask. The gas concentrator distributes gas into the resuscitating device through a substantially elongated member that has a number of perforations at one end and a stopper at an opposite end. In addition, the gas concentrator has one or more air check valves that are in fluid communication with the reservoir of the resuscitating device and the atmosphere. A front manifold is used to couple the reservoir to a patient breather apparatus which regulates the flow of oxygen or gas to the patient.

14 Claims, 8 Drawing Sheets

OTHER PUBLICATIONS

Pulmanex™ "LDS Life Design Systems" (3 pages).
Pall Heat and Moisture Exchanger Filter, "Barrier Filtration for Protection of Patients and Staff from Bacterial and Viral Contamination" (10 pages).
Ohio Medical Products, "Hope Resuscitators" (4 pages).
Laerdal Resuscitators (8 pages).
"Respiratory Care—Tell Them What It's All About" (2 pages).

* cited by examiner

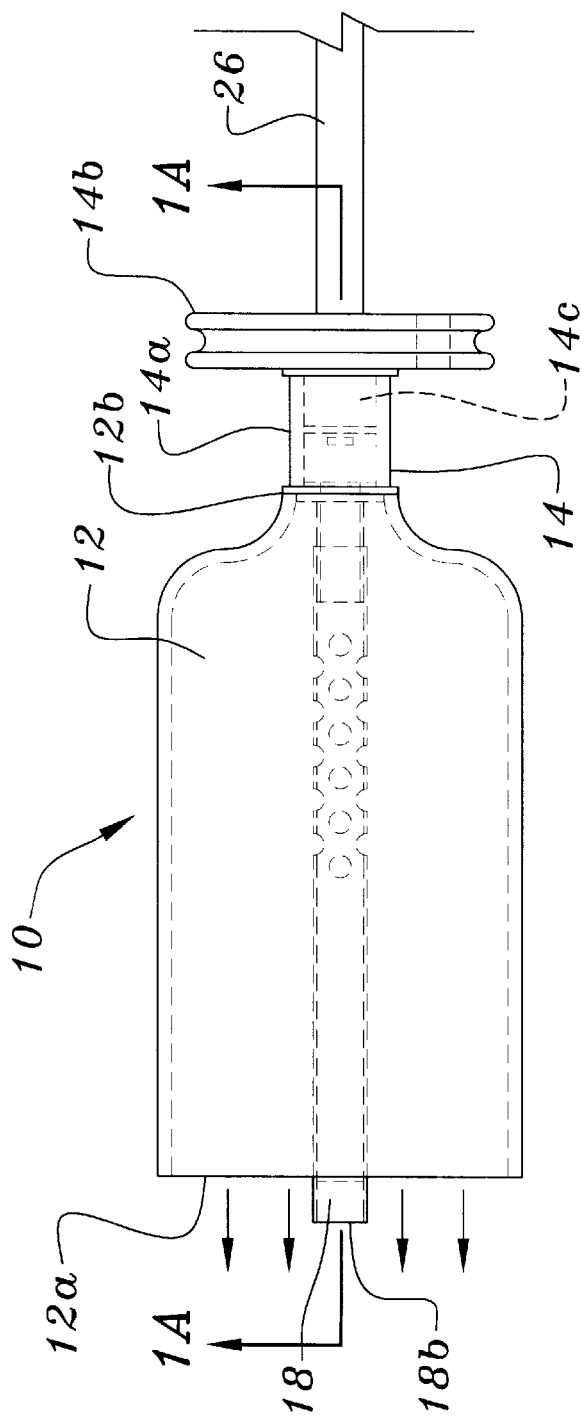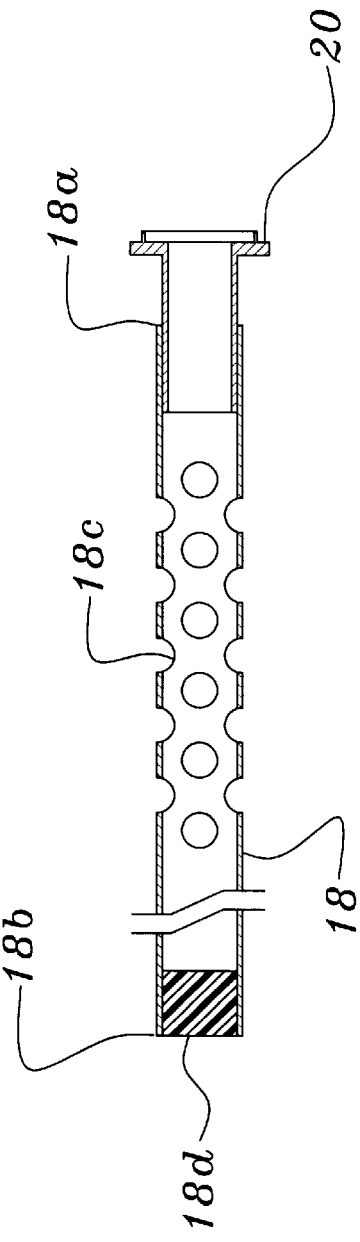

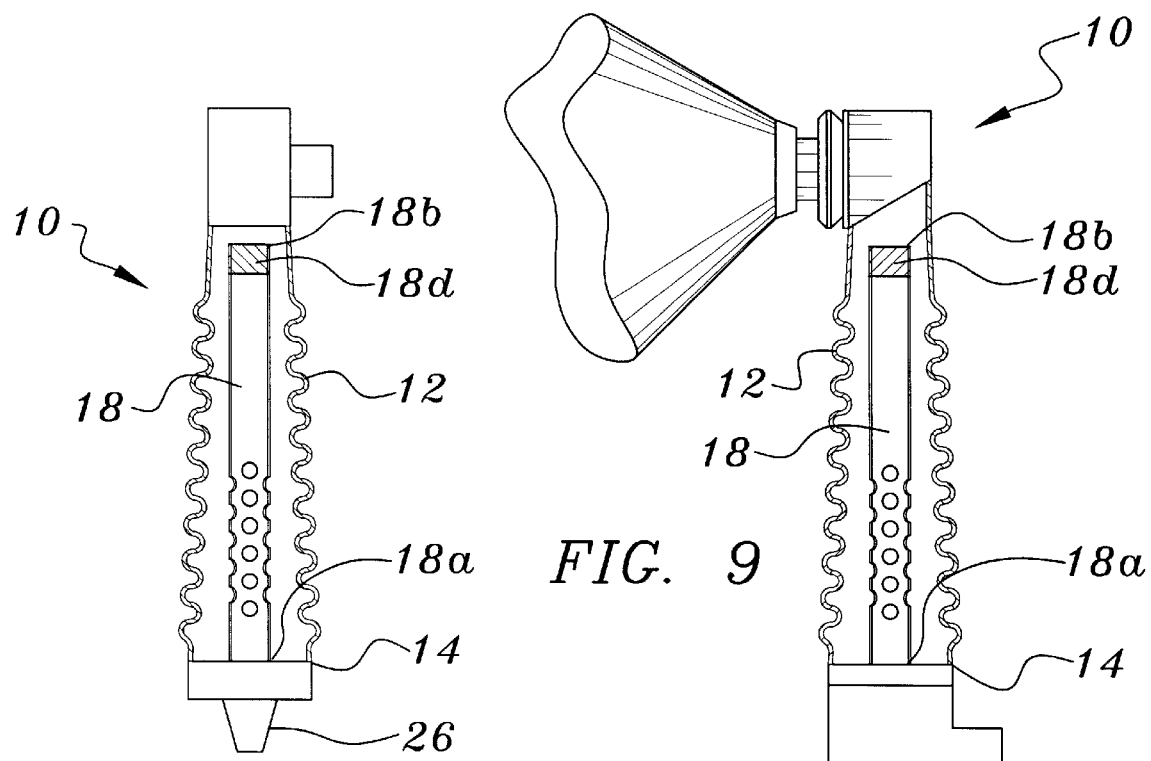
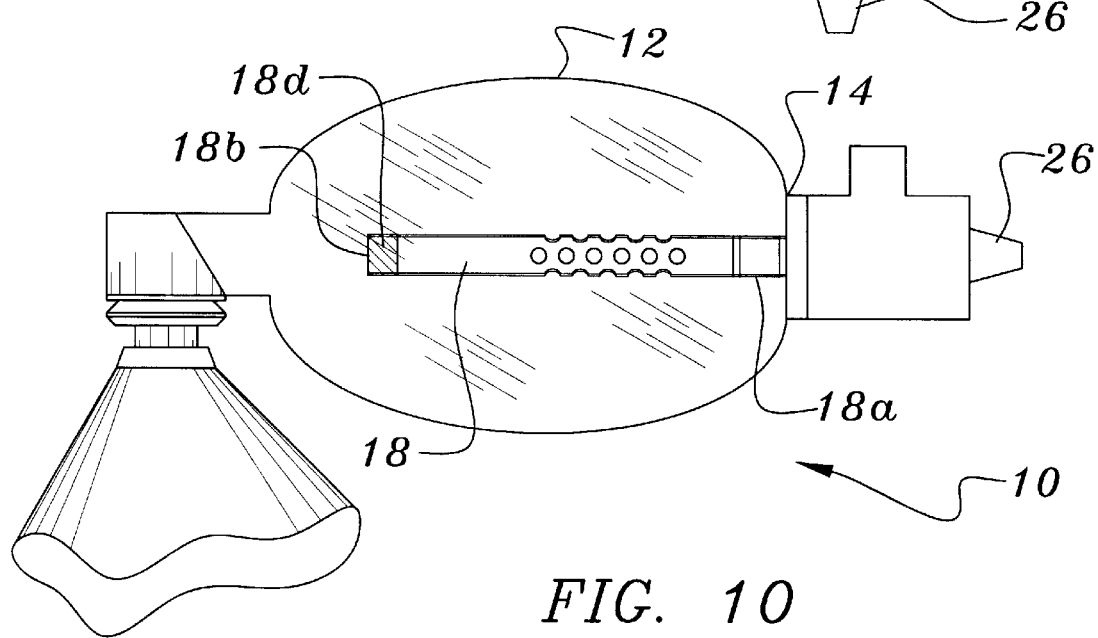

GAS CONCENTRATOR

BACKGROUND OF THE INVENTION

1. Field of the Invention

This invention relates to a gas concentrator, and, more particularly, to an enhanced oxygen/gas concentrator utilizing a unique oxygen/gas concentration device providing instantaneous delivery of rich oxygen/gas concentrations to a patient.

2. Description of the Background Art

Resuscitation devices are used to temporarily emulate a patient's natural breathing. Resuscitation generally refers to externally applied assistance to supplement or restore an individual's respiratory activity. Resuscitation devices force oxygen-air mixtures through a patient's airway system to the lungs at staged intervals, while intermittently applying pressure to the patient's chest cavity inducing exhalation. "Squeeze bag" or "bag-valve-mask" resuscitators make use of some type of manually compressible and self-restoring bag in fluid communication with a face-mask. The operation of prior art resuscitation devices can be broken down into a two step process. First, the mask is applied to the face of a patient while manually squeezing the bag to force air from the bag through the mask and into the patient's lungs. Second, releasing the manually applied pressure from the bag and removing the mask from the patient's face to permit escape of air from the patient's lungs. During this step, the bag would self-inflate with atmospheric air through the mask. The bag would then remain in its restored condition until the next cycle, repeating as necessary. A squeeze bag resuscitator allows a trained person administering treatment to control the quantity and rate of air forced into the patient's lungs.

Squeeze bag resuscitators soon incorporated various refinements. To increase portability and facilitate use by a single person, resilient squeeze bags were adapted to be conveniently held in one hand with the face-masks attached directly to the frontal extremities of the bags. A one-way check valve in fluid communication with the interior of the bag and the atmosphere was introduced to permit refilling of the bag with fresh air during its restoration phase without removing the mask from the face of the patient. Additionally, the patient non-rebreathing valve assembly emerged. The assembly is located between the bag and the mask and permits fresh air to move from the bag into the mask during the squeeze phase, but vents to the atmosphere air returned to the mask from the patient's lungs during the bag restoration phase, preventing passage of the expired air into the bag from which it would be forced back into the patients lungs or "rebreathed" during the next squeeze phase.

During the course of development of squeeze bag type resuscitators, it was recognized that it would be desirable to administer pure oxygen, or at least oxygen enriched air, rather than merely atmospheric air, in treating some resuscitation patients. Accordingly, the development of a practical means for introducing oxygen into the squeeze bag initially entailed providing "oxygen enrichment" for the air drawn into the squeeze bag from the atmosphere during the restoration phase of the bag cycle. A common method for oxygen enrichment is to provide an elongate tube of relatively large diameter having one end in fluid communication with the fill valve opening of the bag and the other end exposed to the atmosphere, together with a considerably smaller tube extending into the larger tube and coupled with a pressurized oxygen source for continuously releasing oxygen into the air entering and accumulating within the large tube from the atmosphere. Such devices are referred to as "oxygen accumulators" and are effective to introduce air-oxygen mixtures into the bag during the restoration phase of its cycle, without significantly increasing the pressure within the bag. Examples of these and other oxygen accumulator resuscitators may be found in U.S. Pat. Nos. 4,501,271, 4,774,941, 4,821,713, 5,067,487, 5,109,840, 5,140,982 and 5,279,289. A shortcoming of resuscitators of this type is that the ambient air can dilute the concentration of the continuously flowing oxygen gas.

In the oxygen accumulator resuscitators described in U.S. Pat. Nos. 4,821,713, 5,067,487 and 5,140,982, two discrete, sequentially operable valves are provided to deliver the air/oxygen mixture, first into the tubular member and then into the face mask. Each valve has a comparatively high spring bias. The first valve can only be opened by releasing the squeeze bag from a compressed state, while the second valve is opened only by squeezing the bag. That is, the patient's spontaneous inspiratory efforts are not capable of operating the valves. This situation is exacerbated by the presence of the mask expiration port that is in direct fluid communication with the atmosphere which assures that insufficient negative inspiratory pressure can be developed in the mask to effect valve actuation.

Furthermore, the advent of the oxygen accumulator squeeze bag resuscitator did not satisfy the need for being able to administer substantially pure oxygen to patients under certain relatively frequently occurring high oxygen demand circumstances, such as resuscitation responsive to cardiac distress or like conditions. The invention disclosed in U.S. Pat. No. 3,796,216 attempts to administer essentially pure oxygen to a patient using a squeeze bag resuscitator. The apparatus included a body member, a squeeze bag, an oxygen inlet, a flapper valve and a face mask. The body member comprises a tubular portion to which the mouth of the squeeze bag is connected. The face mask is joined to the tubular member generally opposite the squeeze bag and an inlet adapted to be connected to a source of breathing gas, such as oxygen, is provided in the tubular member between the squeeze bag and the face mask. The flapper valve regulates passage of oxygen from the squeeze bag to the face mask.

Comparatively, the squeeze bag disclosed in U.S. Pat. No. 3,796,216 is not self-restoring, but is pliable and intended to be continuously inflated with oxygen. When the bag is sufficiently inflated and it is desired to administer oxygen to the patient, the administrator squeezes the bag to increase the pressure in the tubular member to a level sufficient to cause the flapper valve to expose a mask inhalation port and cover a mask exhalation port whereby the oxygen flows into the mask and then to the patient. Once the bag contents are depleted, i.e., the pressure in the body member is insufficient to overcome the bias of the flapper valve, the valve returns to its normal position covering the inhalation port and exposing the exhalation port. At this time, the patient exhales, his expiratory gases pass through the exhalation port and then the bag reinflates. This process is repeated until the patient breathes normally.

However, this type of system is incapable of dispensing pressurized atmospheric air in the event of failure or depletion of the pressurized oxygen supply. Specifically, even if the gas source were disconnected from the gas inlet thereby exposing the inlet to the atmosphere, the squeeze bag is not self-restoring. That is, the squeeze bag cannot create either the negative pressure required to draw air into the inlet or the positive pressure to expel the air. U.S. Pat. Nos. 2,399,643, 2,834,339, 3,196,866, 3,316,903, 3,473,529, 4,037,595, 4,077,404, 4,088,131, and 4,121,580 describe self-distending squeeze bag or similar resuscitators capable of administering air, oxygen or air-oxygen mixtures upon compressing the squeeze bag. Gas flow to and from the patient is effected by the opening and closing of at least one, and usually two or more, spring-biased check valves, flap valves or combinations of both. The resuscitators disclosed in U.S. Pat. Nos. 3,196,866 and 3,316,903 operate such that during expansion of the squeeze bag, the oxygen being supplied to the bag will always be mixed with atmospheric air because the resuscitator valve assembly includes ports in communication with the atmosphere and the interior of the bag, said ports normally being open and can only be closed by squeezing the bag. Thus, these resuscitators may together be envisioned as another form of the "oxygen accumulator" type resuscitators previously discussed. Moreover, resuscitators of this type are incapable of delivering pure oxygen which may at times be vital depending upon the needs of the patient.

Most of the other resuscitators provided in U.S. Pat. Nos. 2,399,643, 2,834,339, 3,473,529, 4,037,595, 4,077,404, 4,088,131 and 4,121,580 may effectively administer substantially pure oxygen. However, the valve assemblies are particularly complex in construction and heavily dependent upon the valve spring biases to effect proper resuscitator operation. Should the oxygen supply of such a resuscitator be temporarily interrupted, the patient would need to expend considerable inspiratory effort to draw atmospheric air into the resuscitator. The patient may be incapable of such exertion and only aggravate the respiratory distress.

Pressurized oxygen cannot easily be continuously introduced into a squeeze bag resuscitator without comprising other essential system functions. To circumvent these problems, assorted valving arrangements have been developed for introducing and interrupting the supply of pressurized oxygen into various parts of the resuscitator system. Such valving arrangements are intended to respond automatically to particular conditions of the resuscitator system, responding to sensing of differential pressures, and are commonly referred to as "demand oxygen supply valves". Despite their effectiveness, the demand oxygen supply valves disclosed are complicated in design and operation, costly to manufacture and, because of their numerous parts, susceptible to malfunction. Should any of these intricately interrelated components fail to function precisely as designed, oxygen administration will be detrimentally affected, if not totally interrupted.

Should the oxygen flow be interrupted for any reason, the patient would have ready access to the atmosphere by simply inhaling, thereby drawing the air through the second flapper valve and then the first flapper valve. To assure that ambient I air does not mix with the oxygen under normal operation, the spring bias of the second flapper valve has been intentionally designed to be rather significant. Because of this built-in bias, however, the patient may experience considerable resistance when it becomes necessary to breathe air directly from the atmosphere. For reasons mentioned above, the patient may not be able to summon the strength to overcome the bias of the second flapper valve and, consequently, the presence of the resuscitator may hinder rather than promote restoration of his normal respiratory activity.

It would be advantageous for a squeeze bag type resuscitator including an uncomplicated, substantially bias-free valve means capable of delivering essentially pure oxygen during normal operation while affording a patient unhindered access to atmospheric air if the oxygen flow ceases.

Apart from the aforementioned deficiencies arising from the construction and/or function of their valve assemblies, optimal performances, versatility and operational convenience of conventional squeeze bag type resuscitator apparatus are encumbered by a number of other component-specific design limitations.

In addition to a squeeze bag, prior art systems include an oxygen reservoir bag upstream of the squeeze bag. The oxygen bag is preferably formed of thin, pliable plastic, which is not self-inflating. The oxygen reservoir bag is generally open at its opposite ends, which are taped or otherwise adhesively and sealingly secured to the upper and lower manifolds. The manifolds are respectively connected to the non-rebreathing valve and the squeeze bag, and are attached to opposite ends of the flexible hose whereby fluid communication is established between the manifolds through the flexible hose. So constructed, the oxygen reservoir bag defines a sealed oxygen chamber about the flexible hose and between the manifolds. A disadvantage of this arrangement is that the additional materials (e.g., tape or adhesive) and attendant labor required to adhesively secure the opposite ends of the oxygen reservoir bag to the manifolds undesirably contribute to the manufacturing cost of the resuscitator. Moreover, if care is not taken in the attachment of the oxygen reservoir bag to the manifolds, oxygen may leak from the system.

U.S. Pat. Nos. 4,917,081 and 4,919,132 teach pliable breathing gas storage bags connected at their opposite ends to components of respiratory apparatus. The bag in U.S. Pat. No. 4,919,132 merely receives smooth tubular inserts having no structure to which the bag may positively and sealingly engage to prevent gas leakage from the bag.

An advantage exists for an improved system by which the oxygen reservoir bag may be sealingly attached to the resuscitator without resort to adhesive tape or other superfluous fastening means. U.S. Pat. No. 4,501,271 illustrates a conventional, fully disposable resuscitator. Such apparatus is designed for one-time use, preventing cross-contamination. However, disposable resuscitators must be discarded in their entirety after a single use. Consequently, these systems are expensive and costly to maintain as inventory. Moreover, because many of the resuscitator components are subject to patient contamination, and are not sterilized after usage, these resuscitators are not considered to be particularly environmentally compatible.

Fully reusable resuscitators, as described in U.S. Pat. No. 2,834,339, are sterilizable and reusable. While these systems appear to be more economical, they require sterilization after each use. Consequently, considerable handling, disassembly, assembly and testing is needed to assure that the system is properly sterilized and continues to function properly.

U.S. Pat. Nos. Re. 24,193, 2,834,399, 3,196,866, 3,473, 529 and 4,374,521 represent examples of squeeze bag resuscitators whose squeeze bags are self-sealingly or "stretchfit" onto the apparatus. None of these disclosures, however, address the economic, environmental and safety advantages that may be achieved through development of a partially reusable resuscitator, particularly one whose squeeze bag may be repeatedly sterilized and reused and whose other components may be discarded after each use.

A further advantage exists, therefore, for a squeeze bag resuscitator that permits ready sterilization and reuse of its most rugged, costly and yet most easily sterilized component, i.e., its squeeze bag, and which simultaneously affords convenient discardability of its other functional components as an integrated disposable assembly.

The present invention overcomes the disadvantages with these prior art systems, and provides a unique oxygen/gas ok concentrator adaptable for use in breathing devices, particularly resuscitators.

An advantage of the present invention is that simpler tooling devices are required to fabricate the manifold and gas distribution means, thereby reducing manufacturing costs.

Another, more specific, advantage of the present invention is to provide increased oxygen/gas concentrations.

Still another, more specific, advantage of the present invention is to provide faster oxygen/gas recovery times during low volumetric flow rates.

Yet another advantage of the present invention is to administer pure oxygen, or at least oxygen enriched air, rather than merely atmospheric air, in the treatment of some resuscitation patients.

Another advantage of the present invention is the ability to dispense pressurized atmospheric air in the event of failure or depletion of the pressurized oxygen supply.

Still another advantage of the present invention is to provide an overall safer breathing apparatus.

Yet another advantage of the present invention is that assembly time is reduced.

Another advantage of the present invention is to provide a more manageable gas concentrator.

Still another, more specific, advantage of the present invention is to provide a more manageable resuscitator.

Yet another advantage of the present invention is to provide a means for distributing gas within a gas reservoir.

Another advantage of the present invention is to provide a manifold within a gas reservoir.

Still another, more specific, advantage of the present invention is to provide a means for supplying a gas to a manifold within a gas reservoir.

Yet another advantage of the present invention is to provide a gas concentrator adaptable for use within a breathing device, comprising an elongate pliable reservoir, including a first opening and a second opening; a manifold including a first part and a second part, said first part being coupled to said second opening of said reservoir; a means for distributing gas throughout said reservoir, wherein said means is substantially encompassed by said reservoir and connected in fluid communication with said manifold; and, a means for supplying gas to said manifold, said supply means being connected and in fluid communication with said manifold, thereby supplying gas to said distributing means.

Another advantage of the present invention is to provide an apparatus for concentrating gas, adaptable for use within a breathing device, comprising an elongate pliable reservoir, including a first opening and a second opening; a manifold including a first part and a second part, said first part being coupled to said second opening of said reservoir; a means for distributing gas throughout said reservoir, wherein said means is substantially encompassed by said reservoir and connected in fluid communication with said manifold; and a means for supplying gas to said manifold, said supply means being connected and in fluid communication with said manifold, thereby supplying gas to said distributing means.

Still another, more specific, advantage of the present invention is to provide a system for concentrating and delivering gas, said system comprising a gas supply; an elongate pliable reservoir including a first opening and a second opening; a manifold including a first part and a second part, said first part being coupled to said second opening of said reservoir, wherein said manifold further comprises a gas check valve and an air check valve, said gas check valve located between and being in fluid communication with said distributing means and said supply means, wherein said air check valve is in fluid communication with the atmosphere, and, wherein said gas check valve and said air check valve manifest an inflow state and a restricted state; a means for distributing gas throughout said reservoir, wherein said distributing means comprises a first end, a sealed second end, and a plurality of uniformly distributed perforations located substantially adjacent to said first end of said distributing means, wherein said first end of said distributing means is connected to said first part of said second manifold, said distributing means being substantially encompassed by said reservoir; and a means for supplying gas to said manifold, said supply means being connected and in fluid communication with said manifold and said gas supply, thereby supplying gas to said distributing means.

The foregoing has outlined some of the pertinent objects of the invention. These objects should be construed to be merely illustrative of some of the more prominent features and applications of the intended invention. Many other beneficial results can be attained by applying the disclosed invention in a different manner or modifying the invention within the scope of the disclosure. Accordingly, other objects and a fuller understanding of the invention and the detailed description of the preferred embodiment in addition to the scope of the invention defined by the claims taken in conjunction with the accompanying drawings.

SUMMARY OF THE INVENTION

An object of the present invention is to provide a unique method for furnishing a substantially instantaneous oxygen/gas flow adaptable for use within known breathing devices. This object is achieved, and disadvantages of prior art approaches are overcome, by providing a novel gas concentrator for producing a substantially instantaneous high concentration oxygen flow to a variety of breathing devices. The gas concentrator includes a unique gas distribution apparatus, a reservoir, a manifold, two or more check valves, and a gas supply means. In one particular aspect of the invention, the gas distribution apparatus comprises an elongated tube sealed at one end, and including a number of uniformly spaced holes located substantially adjacent to the opposite end. The manifold accommodates a variety of components while also serving as a coupler between gas distribution apparatus and gas supply means. An oxygen check valve is located between the gas distribution apparatus and supply means to control the oxygen/gas flow into the gas concentrator. One or more air check valves are included within the manifold which act as a safety mechanism in case the oxygen/gas flow terminates or if a low volumetric oxygen/gas flow rate is encountered. The supply means generally is used to couple an oxygen/gas supply to the manifold for delivering oxygen/gas to the system. The reservoir can be a pliable material which concentrates the distributed gas accumulated from the gas distribution apparatus for delivery to a breathing device.

In a preferred embodiment, the gas concentrator is connected to a resuscitation device. The gas concentrator reservoir is located within an outer reservoir of the resuscitator while the gas distribution means is substantially encompassed by the gas concentrator reservoir.

The reader of this specification will readily appreciate other objections, features and advantages of the present invention.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be had to the following detailed description taken in connection with the accompanying drawings in which:

FIG. 1 is a profile view of a preferred embodiment of a gas concentrator according to the present invention;

FIG. 2 is a profile view of a gas distribution apparatus according to the present invention;

FIG. 9 is a representation of the present invention incorporated into a high concentration gas mask.

FIG. 10 is a representation of the present invention incorporated into an alternative embodiment of a high concentration gas mask.

DETAILED DESCRIPTIONS OF THE PREFERRED EMBODIMENTS

The devices described herein can be disposable or permanent types dependent on the intended application. Permanent or reusable devices are typically manufactured to be easily dismantled for cleaning and sterilization. Disposable units are generally only used once and in some instances used on more than one occasion.

Figure 1A:
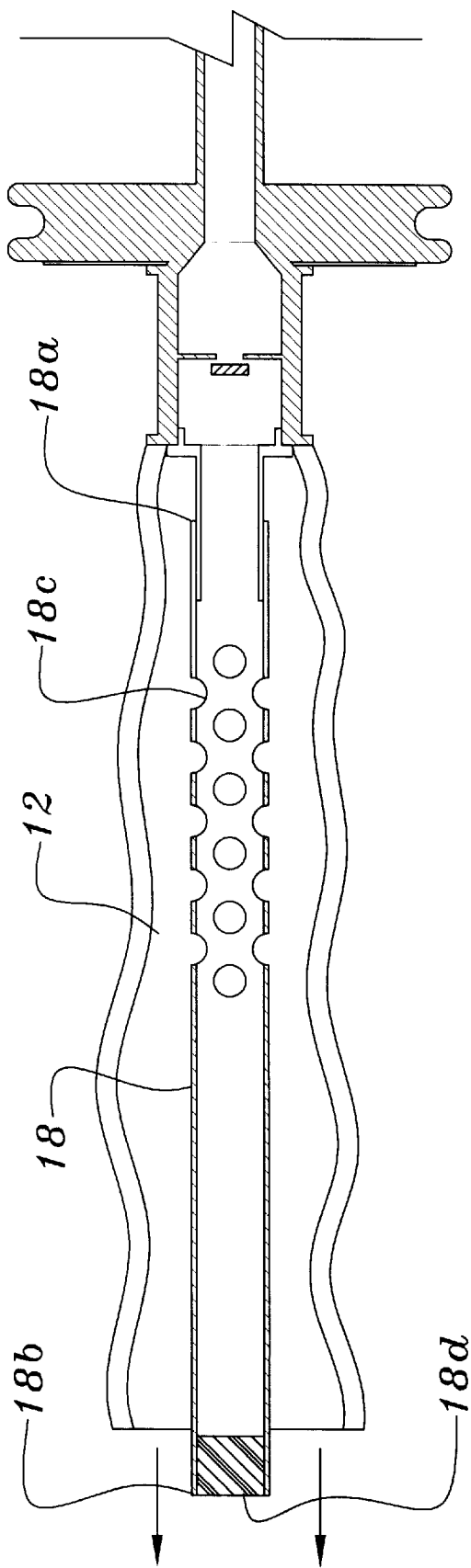
FIG. 1A is a longitudinal cross sectional view of FIG. 1 along lines 1A—1A.
Figure 3:
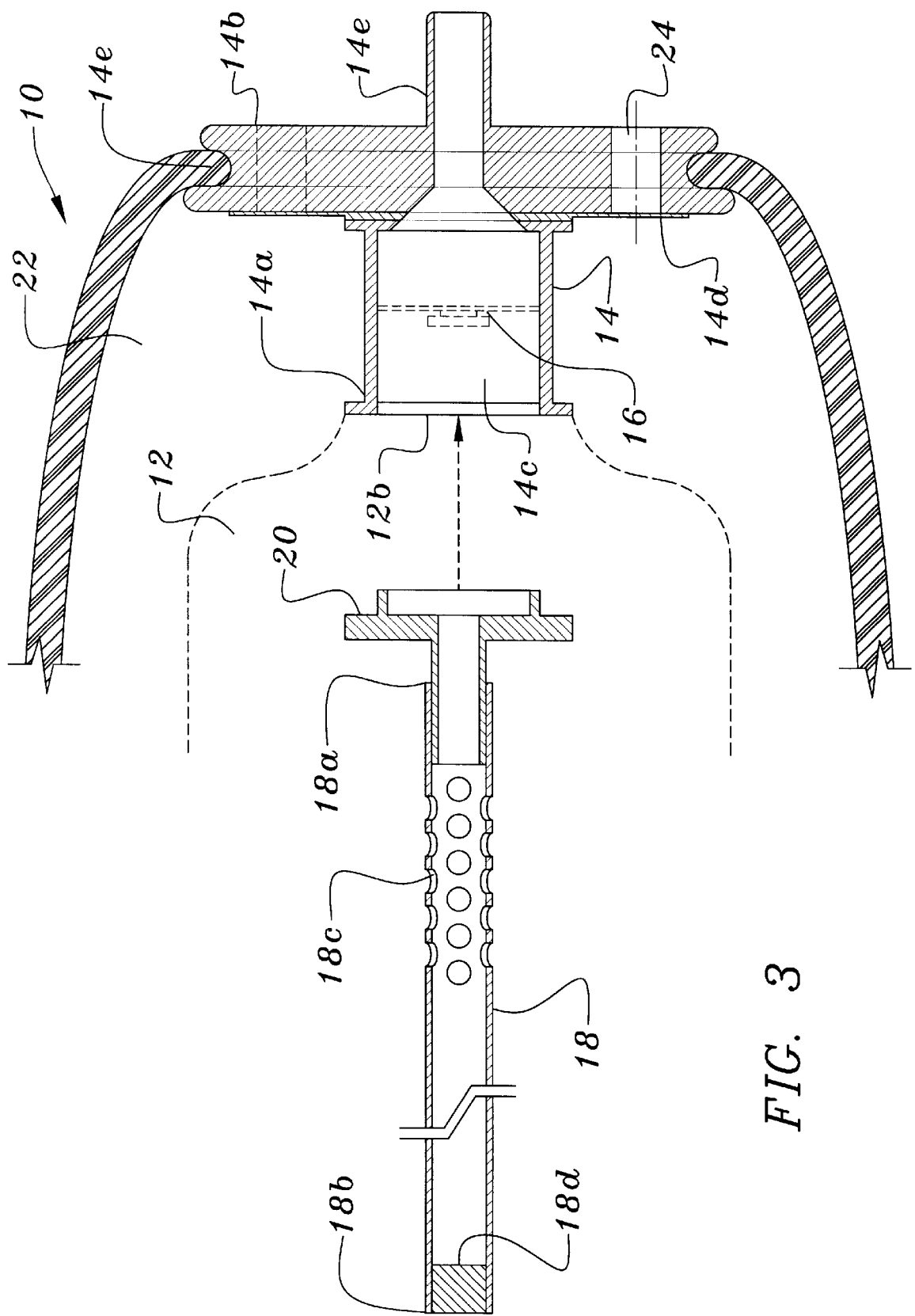
FIG. 3 is an exploded profile view of a gas concentrator according to the present invention.

As shown in FIG. 1, gas concentrator 10 consists of a reservoir 12, which includes a first opening 12a and a second opening 12b. Manifold 14 includes a first part 14a and a second part 14b. First part 14a contains a passageway 14c to accommodate a gaseous flow. As shown in FIG. 3, first part 14a will include a check valve 16 within passageway 14c to control the flow of gas through passageway 14c. In a preferred embodiment, check valve 16 will be a two-state valve. When the pressure within reservoir 12 is lower than atmospheric pressure, check valve 16 allows gas to flow towards reservoir 12. When the pressure within reservoir 12 reaches or exceeds atmospheric pressure, check valve 16 will stop the flow of gas into reservoir 12. Those skilled in the art will recognize the existence of various types of check valve devices that could be utilized in passageway 14c such as a flutter valve, duckbill valve or a spring-loaded type valve. The sensitivity of check valve 16 can be varied to meet a particular design criterion.

Second opening 12b of reservoir 12 is affixed to first part 14a of manifold 14. The resulting connection must be sealed to prevent gas from exiting from the system having a detrimental effect on the efficiency of gas concentrator 10. Those skilled in the art will realize that the connection between first part 14a of manifold 14 to the second opening 12b of reservoir 12 can be made in a variety of ways. A less expensive embodiment for disposable units might utilize tape, glue or a weld to complete the connection. A more expensive connection method used in reusable or permanent devices might utilize a clamp or large o-ring.

Referring to FIGS. 2 and 3, a preferred embodiment for gas distribution means 18 is shown. Gas distribution means 18 includes a first end 18a and a sealed second end 18b. Second end 18b can be sealed with a plug or stopper 18d, or during fabrication. Stopper 18d results in a rapid increase in the fill rate of reservoir 12. Without stopper 18d, gas distribution means 18 fills reservoir 12 at a much slower rate. The length, outer diameter and inner diameters of gas distribution means 18 will vary with each application. As an example, gas distribution means 18 could have a ⅜" outer diameter, a ¼" inner diameter, and a twelve inch length. Generally, gas distribution means 18 will be fabricated from PVC, Tygon, low density polyethylene, or Teflon. As seen in FIG. 1, gas distribution means 18 is shown protruding from the first end 12a of reservoir 12. This protrusion is a safety feature to ensure that reservoir 12 will not collapse upon itself and restrict the flow of gas through gas concentrator 10. As best shown in FIG. 2, gas distribution means 18 contains a number of perforations 18c. Again, the number and size of perforations 18c will vary per application. In a preferred embodiment, perforations 18c will be uniformly staggered holes located substantially adjacent to first end 18a. First end 18a of gas distribution means 18 can be coupled to first part 14a of manifold 14 directly by utilizing tape, glue, weld or a clamp, dependent on whether gas concentrator 10 is disposable or permanent. As shown in FIG. 3, an adapter 20 can also be used to couple gas distribution means 18 to first part 14a of manifold 14.

According to the present invention, a preferred embodiment is shown in FIG. 3, wherein gas concentrator 10 is adaptable for use within a resuscitation type device. First part 14a of manifold 14 will generally be fabricated from a clear, rigid material that can be injection molded, thereby decreasing manufacturing expenses. Some material examples are: K-resin, acrylic, polycarbonate, or nylon. manifold 14 may be configured to accommodate an inner reservoir 12, outer reservoir 22, gas distribution means 18, oxygen check valve 16, and air check valves 24. The second part 14b of manifold 14 is formed to accommodate outer reservoir 22 and, air check valves 24. As shown in FIG. 3, second part 14b comprises an annular platform 14d which further comprises a circumferential channel 14e which, in turn, accepts an end of outer reservoir 22. The end of outer reservoir will be fabricated to sealing fit annular platform 14e or, alternatively, glue, tape or a clamp can be used to affix outer reservoir 22 to second part 14b of manifold 14. Outer reservoir 22 will ideally be fabricated to accommodate a human hand, comprising a non-slip pliable material. Potential reservoir styles are: a knurled/patterned surface that is round, oval, or hexagonal.

Figure 4:
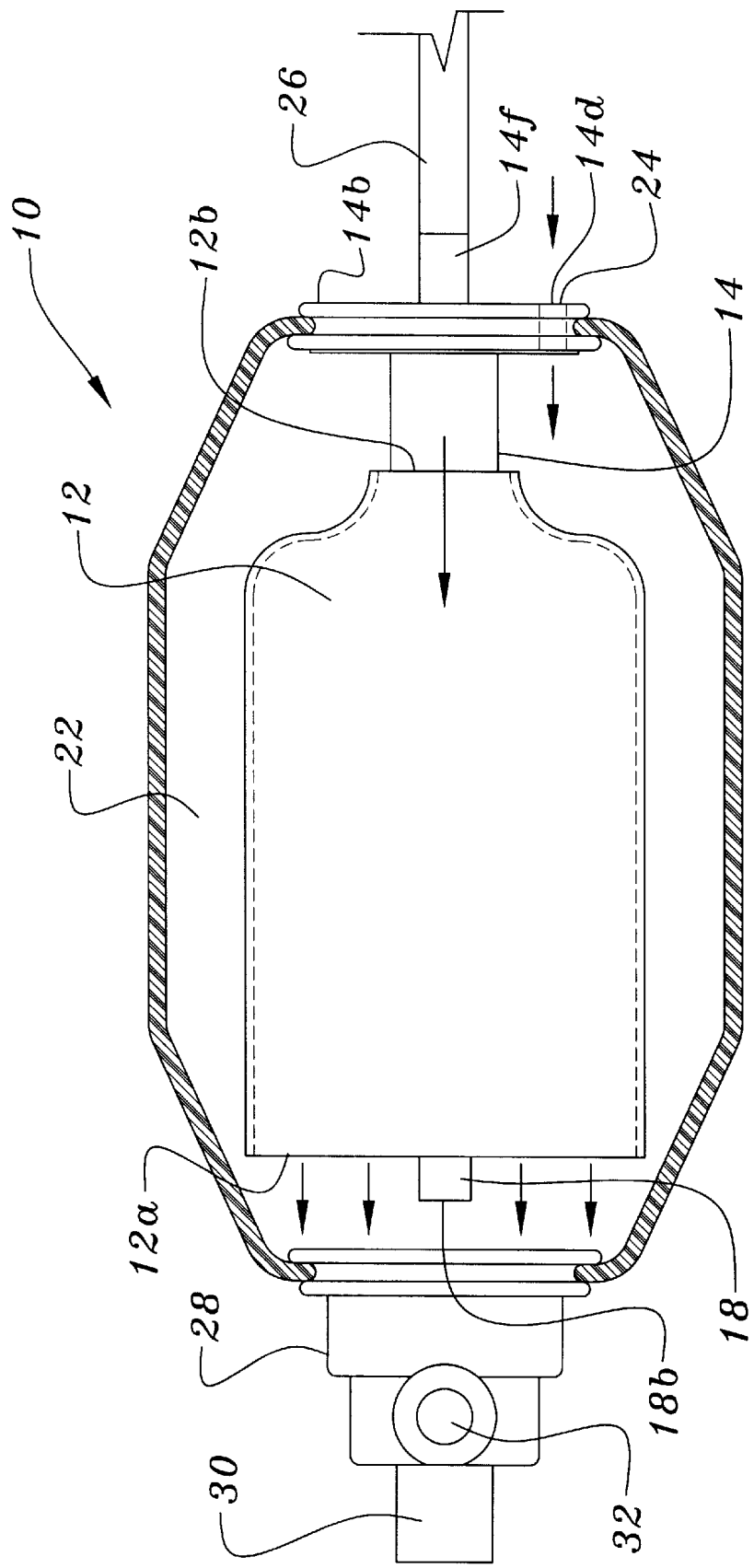
FIG. 4 is a profile view of a gas concentrator within a resuscitation device according to the present invention.

One or more air check valves 24 in fluid communication with the interior of outer reservoir 22 and the atmosphere, may be located within annular platform 14d. As shown in FIG. 4, Second part 14b can also include a stem 14f for acceptance of supply means 26. Alternatively, supply means 26 could be coupled directly to annular platform 14d. A front manifold 28 is used to couple the outer reservoir 22 to a patient breather apparatus which regulates the flow of oxygen or gas to the patient. FIG. 4 shows a two-port front manifold, comprising an inhalation port 30 and an expiration port 32. Front manifold 28 can also contain a similar annular platform as manifold 14 for acceptance of outer reservoir 22. As seen in FIG. 4 inner reservoir 12 is completely encompassed by outer reservoir 22. In a resuscitation type device, first opening 12a will generally encompass a larger volume than second opening 12b of inner reservoir 12. Inner reservoir 12 will typically be composed of similar materials as outer reservoir 22. Locating the inner reservoir 12 within outer reservoir 22 presents an advantage over prior art resuscitation devices which generally have two external reservoirs.

Figure 5:
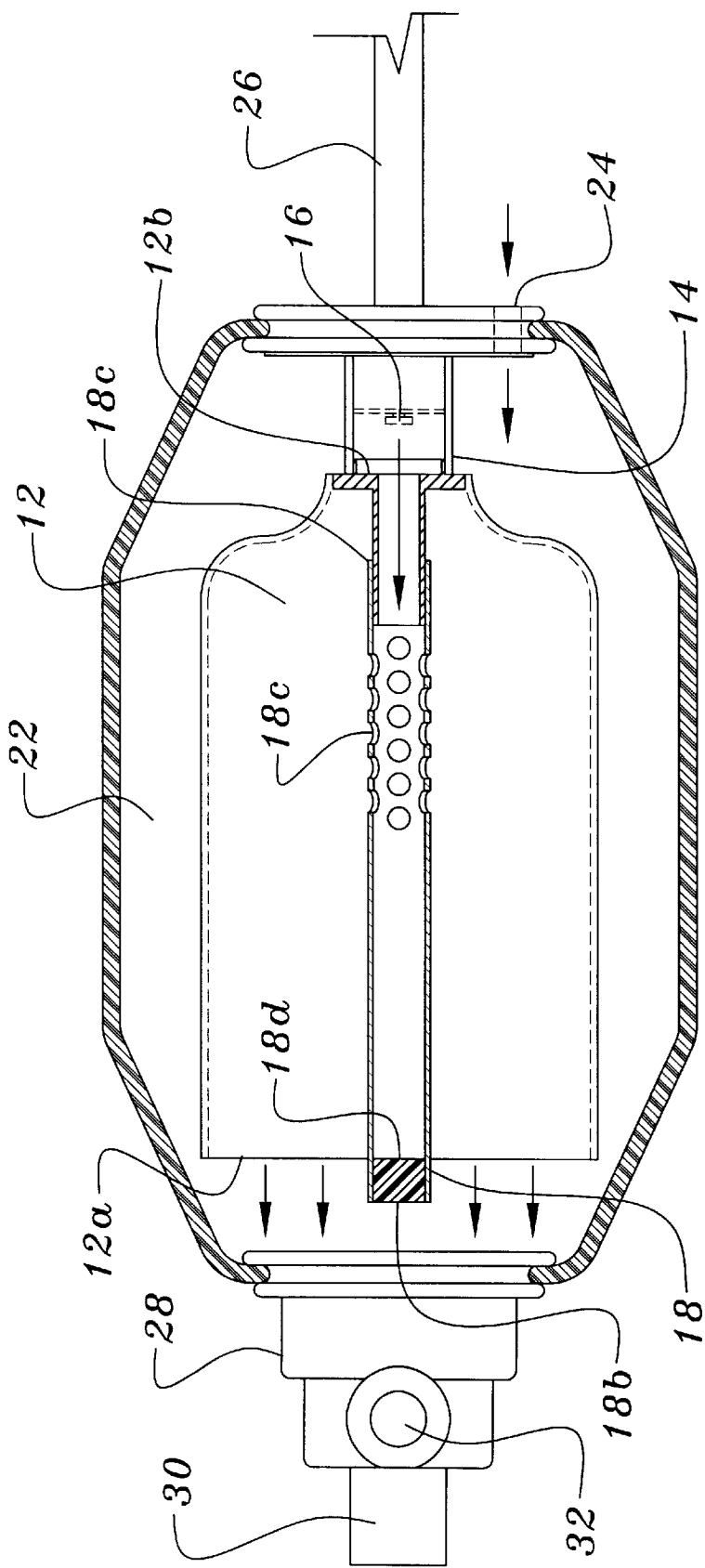
FIG. 5 is a schematic representation of the fill phase of a resuscitator utilizing the gas concentrator according to the present invention.

Resuscitation devices generally have several phases of operation. Phase I, as best shown by FIG. 5, may be a fill phase where inner reservoir 12 is filled with oxygen through gas distribution means 18 which, in turn, is supplied by supply means 26. Stopper 18d located at second end 18b results in a rapid increase in the fill rate of reservoir 12. Gas distribution means 18 will distribute oxygen/gas to the inner reservoir 12 through perforations 18c. Supply means 26 will generally be a flexible tube having a diameter determined by the necessary amount of oxygen to be supplied to the patient. Once inner reservoir 12 is filled, extra oxygen will spill over and continue to fill outer reservoir 22. Air check valve 24 is a safety feature utilized when the oxygen source is depleted or a low volumetric oxygen flow rate exists. Air check valve 24 may be a two-state device, having an open state and a closed state. If oxygen check valve 16 is malfunctioning or the oxygen supply has depleted, i.e., the pressure within reservoir 22 is lower than atmospheric pressure, then air check valve 24 will allow air into reservoir 22. When the pressure within reservoir reaches or exceeds atmospheric pressure, air check valve 24 will close, stopping the flow of air into reservoir 22. Those skilled in the art will recognize the existence of various types of check valve devices that could be utilized. Examples are, flutter valves, duckbill valves or spring-loaded type valves. The sensitivity of air check valve 24 may be varied to meet a particular design criterion.

Figure 6:
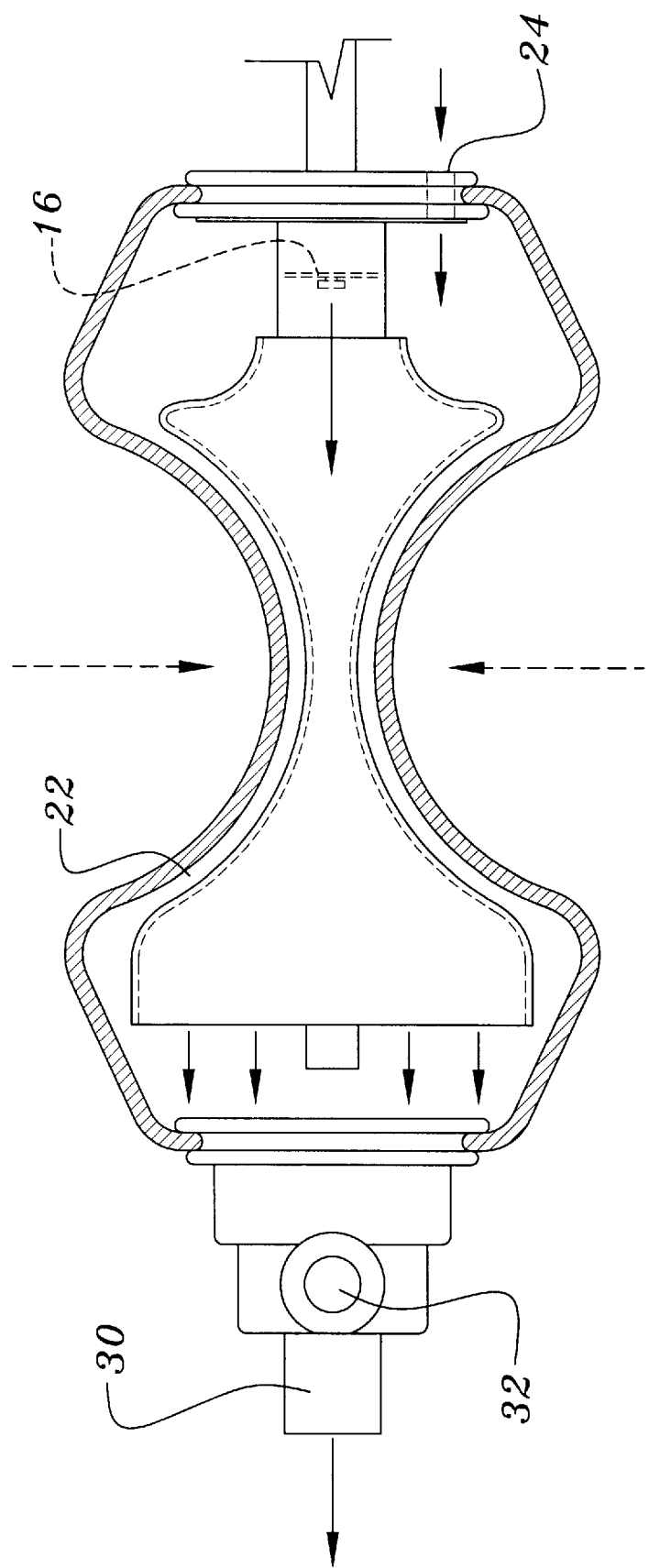
FIG. 6 is a schematic representation of the delivery phase of a resuscitator utilizing the gas concentrator according to the present invention.

Phase II, as best shown by FIG. 6, may be a compression or delivery stage, wherein manual pressure is applied to the surface of outer reservoir 22 to deliver oxygen/gas through the open inhalation port 30 to the patient. During this stage, expiratory port 32 will remain closed. Oxygen check valve 16 and air check valves 24 will be closed due to the positive pressure gradient created within the bag, i.e. the pressure on the inside of check valves 16 and 24 is greater than the pressure on the outside.

Figure 7:
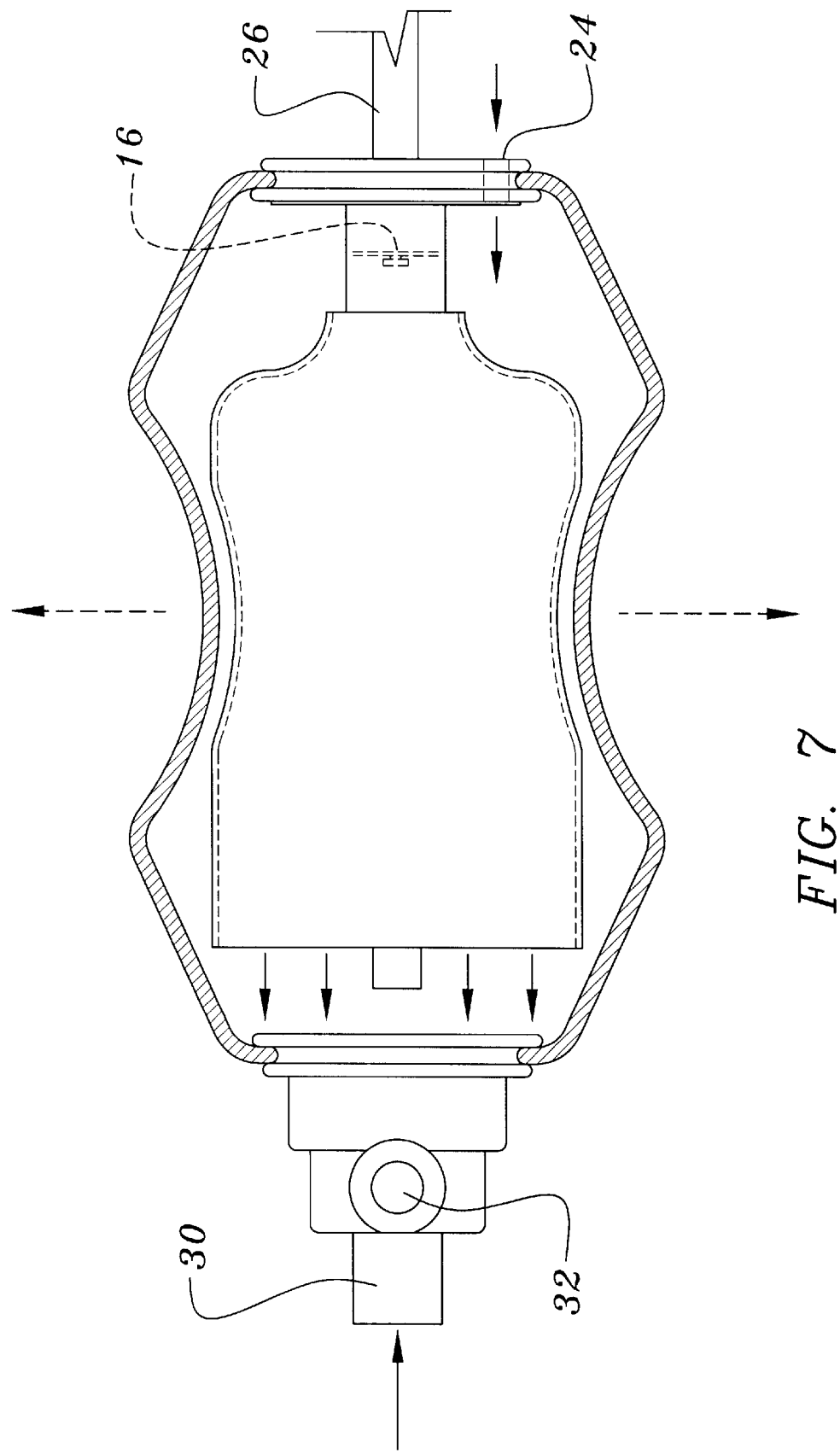
FIG. 7 is a schematic representation of the refill phase of a resuscitator utilizing the gas concentrator according to the present invention; and, FIG. 8 is a representation of the present invention incorporated into a patient tee device.

Phase III, as best shown by FIG. 7, is the refill stage during patient exhalation. During this stage, inhalation port 30 will be closed and expiratory port 32 will open allowing the patient's exhalation to flow to the atmosphere. Also, since there is now a negative pressure gradient within the reservoirs, oxygen check valve 16 will open and oxygen will once again fill the resuscitator. Air check valve 24 will remain closed unless there is an inadequate oxygen flow from supply means 26.

FIGS. 8–10 depict alternative embodiments according to the present invention. Gas concentrator 10 is adaptable for use within a Trach tee, patient tee, or hi-concentration mask. These patient breathing devices operate similarly with gas concentrator 10. Reservoir 12 may be a corrugated tube which encloses gas distribution means 18. Stopper 18d located at second end 18b results in a rapid increase in the fill rate of reservoir 12. First end 18a of gas distribution means 18 will be coupled to a manifold 14 which, in turn, is coupled to supply means 26. For these applications, manifold 14 will usually only be a coupling platform to couple gas distribution means 18 with supply means 26. Supply means 26 will also follow the design discussed previously. The main difference of the aforementioned alternative embodiments is the use of one reservoir compared to the dual reservoir system of the resuscitator.

The present disclosure includes that contained in the appended claims, as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

Now that the invention has been described,

I claim:

1. A gas concentrator adaptable for use within a breathing device, comprising:

an elongate pliable inner reservoir, including a first opening and a second opening;

a manifold including a first part and a second part, said first part being coupled to said second opening of said inner reservoir;

a means for distributing gas throughout said inner reservoir, said means for distributing gas is substantially elongate and comprises a first end having a plurality of perforations, said plurality of perforations are located substantially adjacent to said first end of said means for distributing gas, and a second end having a stopper, wherein said means for distributing gas is substantially encompassed by said inner reservoir and connected in fluid communication with said manifold, and wherein said second end of said means for distributing gas protrudes from said inner reservoir; and a means for supplying gas to said manifold, said supply means being connected and in fluid communication with said manifold, thereby supplying gas to said means for distributing gas.

2. The gas concentrator according to claim 1, wherein said perforations are uniformly distributed, and wherein said second end of said distributing means is sealed.

3. The gas concentrator according to claim 1, wherein said manifold further comprises an air check valve in fluid communication with the atmosphere, said air check valve manifesting an inflow state and a restricted state.

4. The gas concentrator according to claim 1, wherein said manifold further comprises a gas check valve in fluid communication with said distributing means and said supply means, said gas check valve located therebetween and manifesting an inflow state and a restricted state.

5. The gas concentrator according to claim 1, wherein said second part of said manifold comprises an annular platform, wherein the outer circumference of said platform comprises a channel throughout.

6. The gas concentrator according to claim 5, further comprising an outer reservoir, wherein said outer reservoir includes a first opening and a second opening, wherein said second opening being coupled to said channel of said annular platform, and wherein said outer reservoir encloses said inner reservoir.

7. The gas concentrator according to claim 1, wherein said inner reservoir is an elongate pliable receptacle, wherein said first opening is larger than said second opening.

8. An apparatus for concentrating gas, adaptable for use within a breathing device, comprising:
   an elongate pliable inner reservoir, including a first opening and a second opening;
   a manifold including a first part and a second part, said first part being coupled to said second opening of said inner reservoir;
   a means for distributing gas throughout said inner reservoir, said means for distributing gas is substantially elongate and comprises a first end having a plurality of perforations, said plurality of perforations are located substantially adjacent to said first end of said means for distributing gas, and a second end having a stopper, wherein said means for distributing gas is substantially encompassed by said inner reservoir and connected in fluid communication with said manifold, and wherein said second end of said means for distributing gas protrudes from said inner reservoir; and
   a means for supplying gas to said manifold, said supply means being connected and in fluid communication with said manifold, thereby supplying gas to said means for distributing gas.

9. The apparatus for concentrating gas according to claim 8, wherein said perforations are uniformly distributed, and wherein said second end of said distributing means is sealed.

10. The apparatus for concentrating gas according to claim 8, wherein said manifold further comprises an air check valve in fluid communication with the atmosphere, said air check valve manifesting an inflow state and a restricted state.

11. The apparatus for concentrating gas according to claim 8, wherein said manifold further comprises a gas check valve in fluid communication with said distributing means and said supply means, said gas check valve positioned therebetween, manifesting an inflow state and a restricted state.

12. The apparatus for concentrating gas according to claim 8, wherein said second part of said manifold comprises an annular platform, wherein the outer circumference of said platform comprises a channel throughout.

13. The apparatus for concentrating gas according to claim 8, wherein said inner reservoir is an elongate pliable receptacle, wherein said first opening is larger than said second opening.

14. A system for concentrating and delivering gas, said system comprising:
   a gas supply;
   an elongate pliable inner reservoir including a first opening and a second opening; and
   a manifold including a first part and a second part, said first part being coupled to said second opening of said inner reservoir, wherein said manifold further comprises a gas check valve and an air check valve, said gas check valve located between and being in fluid communication with a means for distributing gas throughout said inner reservoir and a means for supplying gas to said manifold, wherein said air check valve is in fluid communication with the atmosphere, wherein said gas check valve and said air check valve manifest an inflow state and a restricted state, wherein said distributing means comprises a first end, a sealed second end, and a plurality of uniformly distributed perforations located substantially adjacent to said first end of said distributing means, wherein said first end of said distributing means is connected to said first part of said second manifold, said distributing means being substantially encompassed by said inner reservoir, and
   said supply means being connected and in fluid communication with said manifold protrudes from said inner reservoir, and said gas supply, thereby supplying gas to said distributing means.

* * * * *

UNITED STATES PATENT AND TRADEMARK OFFICE
CERTIFICATE OF CORRECTION

PATENT NO. : 6,253,767 B1
DATED : July 3, 2001
INVENTOR(S) : Mantz, Robert F.

Page 1 of 1

It is certified that error appears in the above-identified patent and that said Letters Patent is hereby corrected as shown below:

Column 3,
Line 52, after "ambient" delete "l".

Column 5,
Line 2, after "oxygen/air" delete "ok".

Column 8,
Line 56, delete "manifold" and insert -- Manifold --.

Column 9,
Line 7, delete "Second" and insert -- second --.

Column 12,
Line 36, after "manifold" insert -- wherein said second end of said distributing means protrudes from said inner reservoir, --.
Line 39, after "manifold" delete "protrudes from said inner".
Line 40, delete "reservoir,".

Signed and Sealed this

First Day of January, 2002

Attest:

Attesting Officer

JAMES E. ROGAN
*Director of the United States Patent and Trademark Office*